United States Patent [19]

Schoolman

[11] Patent Number: 4,706,117
[45] Date of Patent: Nov. 10, 1987

[54] STEREO LASER DISC VIEWING SYSTEM

[76] Inventor: Arnold Schoolman, 6700 Troost, Suite 144, Kansas City, Mo. 64131

[21] Appl. No.: 810,870

[22] Filed: Dec. 17, 1985

Related U.S. Application Data

[63] Continuation-in-part of Ser. No. 616,385, Jun. 1, 1984, Pat. No. 4,559,555, which is a continuation-in-part of Ser. No. 351,917, Feb. 24, 1982, abandoned.

[51] Int. Cl.[4] .................... H04N 5/85; H04N 13/04
[52] U.S. Cl. .................................. 358/88; 358/102; 369/44
[58] Field of Search ............... 358/88, 91, 92, 102, 358/104, 3; 352/239, 102, 103; 369/32, 44

[56] References Cited

U.S. PATENT DOCUMENTS

| | | | |
|---|---|---|---|
| 2,995,156 | 10/1960 | Heilig | 358/88 |
| 3,049,588 | 8/1962 | Barnett | 358/88 |
| 3,404,224 | 10/1968 | Revolo | 352/103 |
| 3,504,122 | 3/1970 | Ratliff | 358/88 |
| 3,527,880 | 9/1970 | Gordon | 358/88 |
| 3,670,097 | 6/1972 | Jones | 358/91 |
| 3,674,921 | 7/1972 | Goldsmith | 358/3 |
| 3,784,738 | 1/1974 | Natter | 358/88 |
| 3,833,300 | 9/1974 | Rymes | 358/250 |
| 3,883,689 | 5/1975 | Mansour et al. | 358/227 |
| 3,919,475 | 11/1975 | Dukich et al. | 358/210 |
| 3,923,370 | 12/1975 | Mostrom | 350/294 |
| 3,932,699 | 1/1976 | Tripp | 358/91 |
| 3,940,204 | 2/1976 | Wirthrington | 350/3.72 |
| 3,976,840 | 8/1976 | Cleveland et al. | 354/900 |
| 4,028,725 | 6/1977 | Lewis | 358/103 |
| 4,034,401 | 7/1977 | Mann | 358/93 |
| 4,051,534 | 9/1977 | Dukich et al. | 358/210 |
| 4,094,010 | 6/1978 | Pepperl | 369/44 |
| 4,094,013 | 6/1978 | Hill | 369/32 |
| 4,115,802 | 9/1978 | Kramer et al. | 358/93 |
| 4,138,741 | 2/1979 | Hedlund | 369/44 |
| 4,153,913 | 5/1979 | Swift | 358/93 |
| 4,160,263 | 7/1979 | Christy et al. | 358/1 |
| 4,242,703 | 12/1980 | Tsuboshima et al. | 358/150 |
| 4,246,607 | 1/1981 | Uijuerberg | 358/111 |
| 4,247,908 | 1/1981 | Lockhart, Jr. et al. | 358/900 |
| 4,266,271 | 5/1981 | Chamoff et al. | 358/200 |

(List continued on next page.)

FOREIGN PATENT DOCUMENTS 56-141690 11/1981 Japan ......................... 358/88
2085692 4/1982 United Kingdom ............ 358/88

OTHER PUBLICATIONS

"Technique Benefits Novice Technicians", *Aviation Week and Space Technology*, Oct. 11, 1982, pp. 133 and 134.
"Video Recording Systems", Kurt F. Wallace, *Electronics Engineers Handbook*, Second Edition, 1982, McGraw-Hill, New York, Sections 68–92.
"Camcorders: Home Movies Made Simple", Mark Schubin, *High Technology*, Oct. 1985, pp. 16–20.

*Primary Examiner*—Howard W. Britton
*Attorney, Agent, or Firm*—Litman, McMahon & Brown

[57] ABSTRACT

A portable television playback system includes a video source unit, video processing circuitry, audio processing circuitry, and a stereo viewing and sound unit. The video source unit is a television receiver, a small videocassette tape cartridge player, or a stereo optical video disc player. The viewing and sound unit has stereoscopic and stereophonic capabilities and is generally a head worn unit having right and left image display devices and right and left earphones. The video and audio processing circuits receive the signals from the video source unit and parallel the video and audio signals to drive the stereo output devices if the source is a television receiver or a videocassette tape player or perform demultiplexing functions to separate the right and left video and audio signals from the right and left multiplexed video/audio signals. The video source unit and the video and audio processing circuits are packaged in a single portable case which may be connected to the head worn viewing and sound unit by an appropriate cable for use.

22 Claims, 10 Drawing Figures

U.S. PATENT DOCUMENTS

| | | | |
|---|---|---|---|
| 4,277,837 | 7/1981 | Stuckert | 358/900 |
| 4,298,176 | 11/1981 | Kendall | 358/88 |
| 4,345,315 | 8/1982 | Cadotte et al. | 364/900 |
| 4,347,508 | 8/1982 | Spooner | 358/250 |
| 4,359,762 | 11/1982 | Stollorz | 360/98 |
| 4,360,875 | 11/1982 | Behnke | 364/900 |
| 4,367,503 | 1/1983 | Treseder | 360/98 |
| 4,395,731 | 7/1983 | Schoolman | 358/88 |
| 4,398,799 | 8/1983 | Swift | 350/174 |
| 4,402,025 | 8/1983 | Anderson et al. | 360/98 |
| 4,504,879 | 3/1985 | Toldi et al. | 360/105 |
| 4,510,525 | 4/1985 | Kuperman et al. | 358/88 |
| 4,524,399 | 6/1985 | Jepsen | 360/97 |
| 4,525,829 | 6/1985 | Affolter | 369/284 |
| 4,527,264 | 7/1985 | d'Arc | 369/77.1 |
| 4,527,265 | 7/1985 | d'Arc | 369/244 |
| 4,531,206 | 7/1985 | Kimura | 369/44 |
| 4,535,434 | 8/1985 | Kishi | 369/111 |
| 4,535,489 | 8/1985 | Satoh | 369/275 |
| 4,536,801 | 8/1985 | Torkelson et al. | 358/280 |
| 4,536,805 | 8/1985 | Maeda | 360/14.1 |
| 4,536,863 | 8/1985 | Giddings | 369/43 |
| 4,536,864 | 8/1985 | Van Rosmalen | 369/44 |
| 4,536,866 | 8/1985 | Jerome et al. | 369/112 |
| 4,536,868 | 8/1985 | Lange et al. | 369/284 |
| 4,536,869 | 8/1985 | Chandler et al. | 369/287 |
| 4,538,181 | 8/1985 | Taylor | 358/208 |
| 4,559,555 | 12/1985 | Schoolman | 358/88 |
| 4,567,532 | 1/1986 | Baer | 358/342 |
| 4,571,628 | 2/1986 | Thornton | 358/88 |
| 4,636,866 | 1/1987 | Hattori | 358/88 |

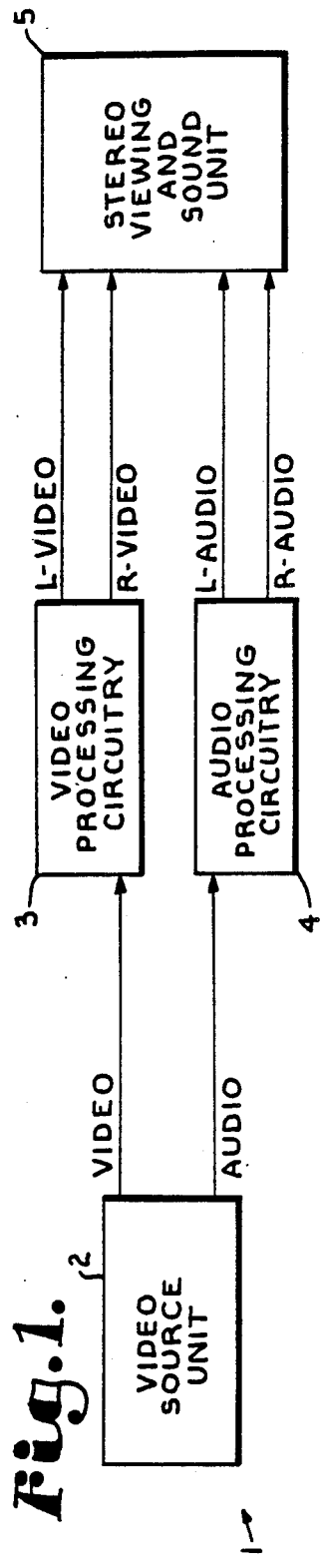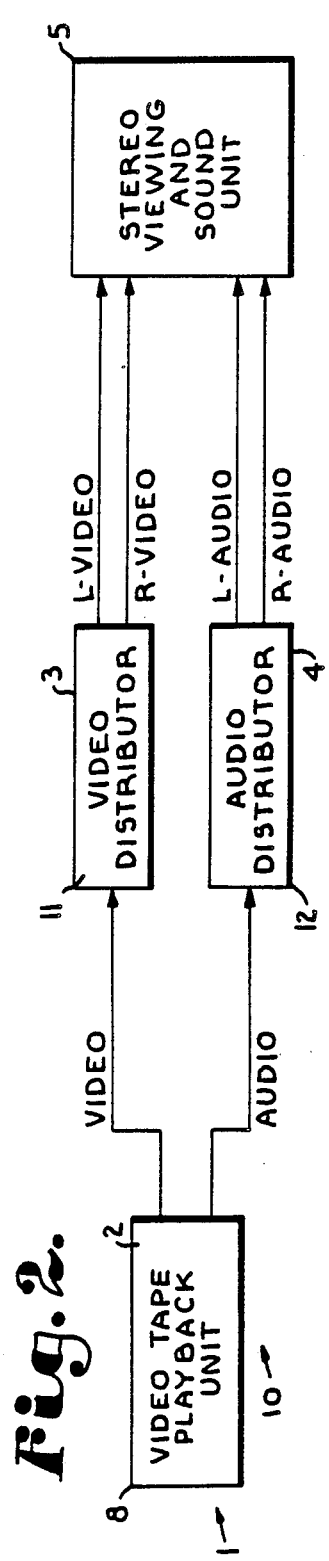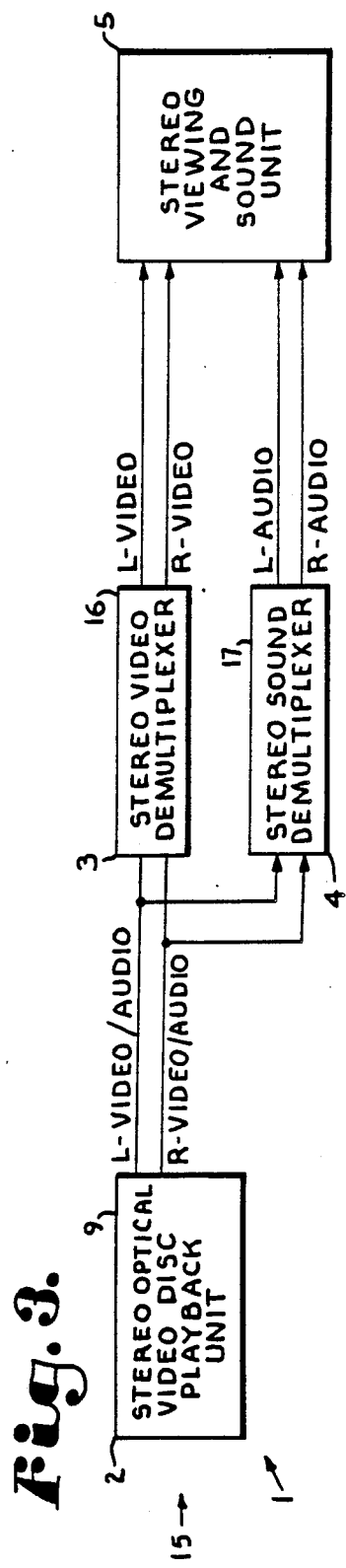

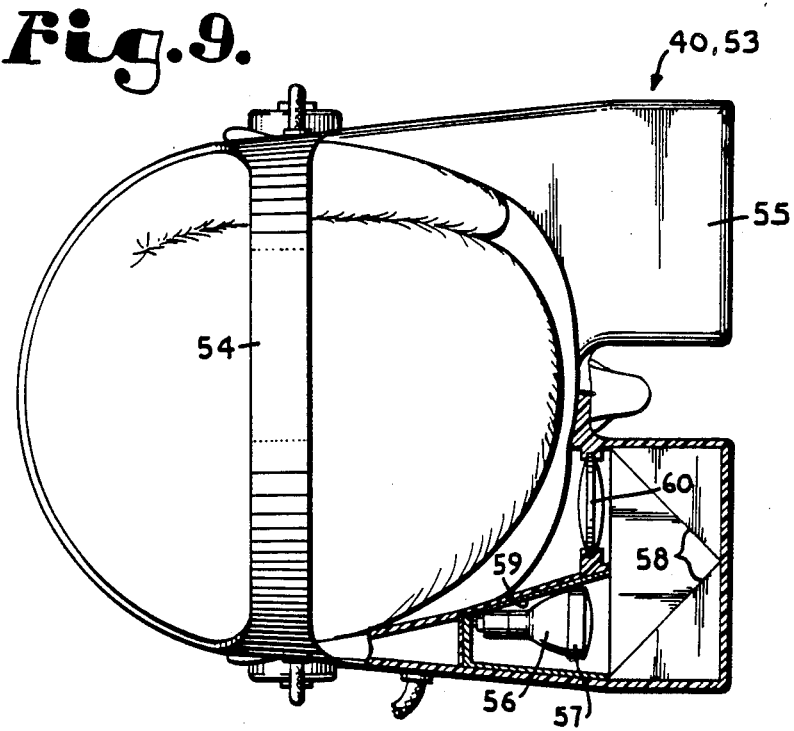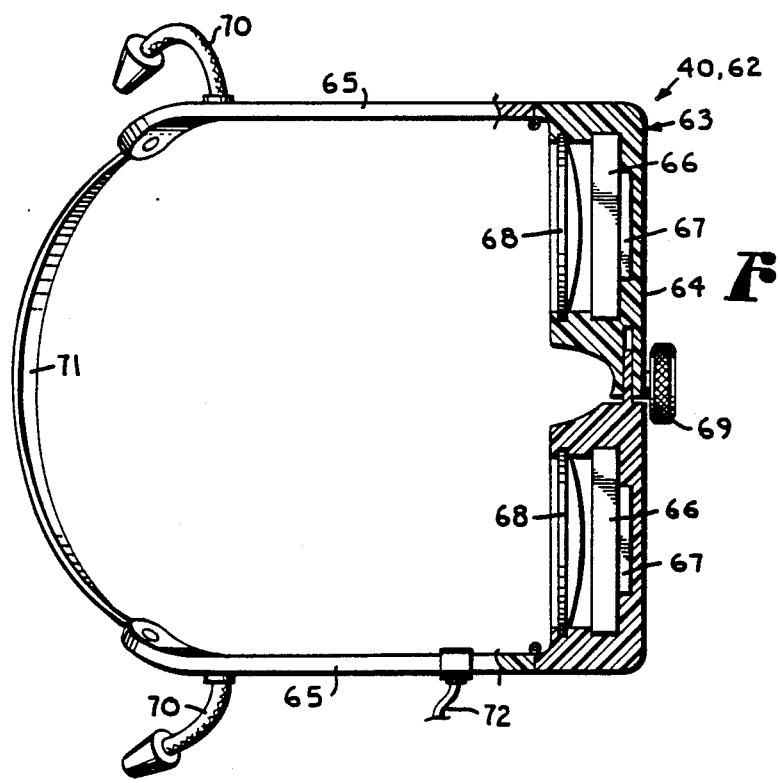

STEREO LASER DISC VIEWING SYSTEM

CROSS-REFERENCE TO RELATED APPLICATIONS

The present invention is a continuation-in-part of application Ser. No. 616,385 filed June 1, 1984, for STEREOSCOPIC REMOTE VIEWING SYSTEM which is now U.S. Pat. No. 4,559,555, which was a continuation-in-part of application Ser. No. 351,917 filed Feb. 24, 1982, for PORTABLE REMOTE TERMINAL WITH HEAD HELD DISPLAY and which is now abandoned, both of which are incorporated herein by reference.

BACKGROUND OF THE INVENTION

The state of the art of portable television devices has progressed from thirty to fifty pound black and white units of the 1950's having twelve inch screens through modern color units of similar weight and having nineteen inch screens. In addition to these "portables" of relatively gigantic proportions which are more properly termed "transportable" or "mobile", there have been easily carried units with screens ranging down to about one and a half inches for black and white screens and about three inches for color screens. The reductions in size for portable televisions and the increase in picture quality has been the result of the trend away from tube type circuitry to transistor circuitry and more recently to integrated circuitry, in addition to decreases in the sizes of picture tubes.

The current trend in portable televisions is toward almost pocket sized units which employ integrated circuitry and so-called flat panel displays. There are several types of flat panel displays available and under development including, for television purposes, flattened cathode ray tubes (CRT's) and various types of monochromatic and color liquid crystal displays (LCD's).

In one type of flattened CRT, the phosphor screen is positioned at an angle to the electron beam and is viewed from the surface struck by the beam. Less power is required for such CRT's than for conventional CRT's since it is not necessary for the phosphors to be excited to a level required for the glow to penetrate to the other side of the phosphor layer. In color LCD's, the image is formed by an array of transparent picture elements or pixels, each pixel comprising a triad of a red, a green, and a blue element. Early LCD's had only an ON state and an OFF state; however, newer displays are capable of a range of densities from off to on, a gray scale in photographic terms. Since LCD's do not generate their own light, backlighting is required for viewing the displayed image.

There are trade-offs in the advantages of one flat screen technology over the other. The LCD's require much less power than the flattened CRT's since it is not necessary to generate an electron beam and since LCD's are inherently low power devices. However, while the scan generating circuitry of flattened CRT's is nearly conventional requiring a slight modification for the orientation of the screen, the image generation for LCD's is much more complex, requiring sequential addressing of the pixels and a required voltage level. Currently, the image quality of flattened CRT's is generally superior to that of LCD's.

Regardless of the type of image display device, current portable televisions do not differ in overall concept from conventional television sets: namely, a television receiver with one screen and one speaker. While there have been a few attempts to include stereophonic sound on video broadcasts, the practice is not widespread. And while videocassette recorders (VCR's) may be played through most televisions, it is necessary to modulate a carrier signal which can be tuned by the television receiver and then down convert and detect the program signal. These extra signal processing stages introduce noise resulting in the degradation of the quality of the recorded video signal.

The art of recording television signals has similarly progressed from a two inch magnetic tape format in broadcasting studios only to the current half inch and eight millimeter videocassette recorder formats available for home use. One of the latest developments in video recording is the emergence of the so-called "camcorder" which is a video camera and recording system in one unit. In contrast to earlier systems in which the camera fed a video signal to a separately packaged recorder unit which contained a full sized videocassette, the camcorders employ videocassettes of reduced size such that the entire camera, recorder, and cassette package are only slightly larger than previous videocassette cartridges.

In addition to the magnetic tape recording of television signals, there have been developments in the recording of such signals on nonmagnetic discs in much the same manner that musical performances are recorded on phonograph records. In one video disc format, the signal is recorded as a spiral groove on the surface and is read by a stylus as with phonograph records. In another video disc format, the signal is recorded as a spiral track of reflective depressions or pits which are read optically by a laser beam. One major advantage of an optically read disc is that there is no wear of the medium as it is read as occurs with magnetic tapes and groove type discs. The majority of current video discs have a diameter of twelve inches. There are currently several commercially available video discs having smaller diameters including approximately ten inches and eight and one half inches.

In the field of sound recording, a recent development is the compact digital audio disc. Compact discs have a diameter of less than five inches and are written and read in much the same manner as optical video discs. However, the sound signal is encoded digitally which greatly reduces the noise content and allows much greater dynamic range than can be accomplished in magnetic recording and in groove type phonograph records. Because of the small size of the compact disc medium and their playerback devices and because of developments in the tracking mechanisms therefor, compact disc players are now available in portable models.

SUMMARY OF THE INVENTION

The present invention joins many of the state of the art video technologies to provide a personal, portable televison playback system with a number of advantages over previously available television systems. One prominent feature of the present invention is the provision of a head worn viewing and sound unit which includes a pair of image display devices and stereophonic earphones. The image display devices can either be fed the same video signals for conventional monoscopic viewing and for compatability with existing monoscopic video sources or they can be fed right and left components of stereoscopically recorded images.

One contemplated video source is a miniature portable videocasette tape playback unit using one of the cassette formats used in camcorders. The tape playback unit is housed in case with a shoulder strap or a loop for attachment to a waist worn belt. The unit also includes video distributor circuits for feeding the video signal to right and left video monitor circuits which drive the image display devices in the head unit. Similar audio processing circuits are provided for driving the earphones of the head unit. The tape playback unit could also easily house a miniature television receiver which could be selected as a video source instead of a prerecorded tape.

A preferred video source is a portable optical video disc player unit having stereoscopic capabilities. The optical video disc player unit is housed in a case somewhat larger that the tape playback unit, although still easily portable. The video disc player unit is adapted to optically read disc media on which tracks on opposite sides of the disc are encoded respectively with right and left components of stereoscopic images and stereophonic sound. In each track, the video signal and audio signal are multiplexed in a standard format. The player unit includes demultiplexer circuitry for separating the right and left video and audio signals along with video monitor circuitry and audio power amplifiers for deriving driving signals for the right and left image display devices and earphones.

The portable television playback system, in addition to home use, could be used while travelling to pass the time, such as by passengers in automobiles, buses, and with appropriate certification on aircraft. In addition to such entertainment uses, the system could be employed for such uses as audio/visual repair instructions for technologically complex systems in the field, in such fields as teaching surgical procedures and for listing and reading library indexes for facilitated research. For such non-entertainment uses, the three dimensional video would speed orientation of the viewer with respect to the image as compared with one dimensional printed or televised images.

OBJECTS OF THE INVENTION

The principal objects of the present invention are: to provide an improved portable television playback system; to provide such a system including a stereoscopic image display and stereophonic sound; to provide such a system including a head worn viewing and sound unit including a pair of image display devices positioned to optically transmit images displayed thereon into the eyes of the viewer and including earphones mounted on the head worn unit; to provide such a system in which the image display devices are color liquid crystal displays; to provide a modified embodiment of such a system wherein the image displays are miniature color cathode ray tubes whose images are reflected into the eyes of the viewer; to provide such a system in which the signal source for the head worn unit is a portable optical video disc playback unit; to provide such a system wherein the video disc playback unit has a pair of read heads which simultaneously read both sides of a video disc on which are optically recorded right and left components of stereoscopic images and stereophonic sound; to provide such a system which is also capable of playing monoscopic video signals and monophonic audio signals such as those derived from conventional video cassette tapes and television receivers; to provide such a system including a stereo optical video disc playback unit capable of playing conventionally recorded discs having monoscopic and monophonic signals thereon as by playing one side then the other side without turning the disc medium over; and to provide such a portable television playback system which is economical to manufacture, durable and precise in operation, and which is particularly well adapted for its intended purpose.

Other objects and advantages of the present invention will become apparent from the following description taken in conjunction with the accompanying drawings wherein are set forth, by way of illustration and example, certain embodiments of this invention.

The drawings constitute a part of the specification, include an exemplary embodiment of the present invention, and illustrate various objects and features thereof.

BRIEF DESCRIPTION OF THE DRAWINGS

FIG. 1 is a block diagram of a generalized portable television playback system according to the present invention.

FIG. 2 is a block diagram of such a system employing a videocassette player as a program source.

FIG. 3 is a block diagram of such a system employing a stereo optical video disc player as a program source.

FIG. 9 is a top plan view of a second embodiment of the stereo viewing and sound unit with a portion broken away to illustrate cathode ray tubes employed as image display devices and prisms to reflect the images to the eyes of the viewer.

FIG. 10 is a top plan view of a third embodiment of the stereo viewing an sound unit of the present invention in the form of a pair of spectacles with a portion broken away to illustrate details.

DETAILED DESCRIPTION OF THE PREFERRED EMBODIMENTS

Figure 4:
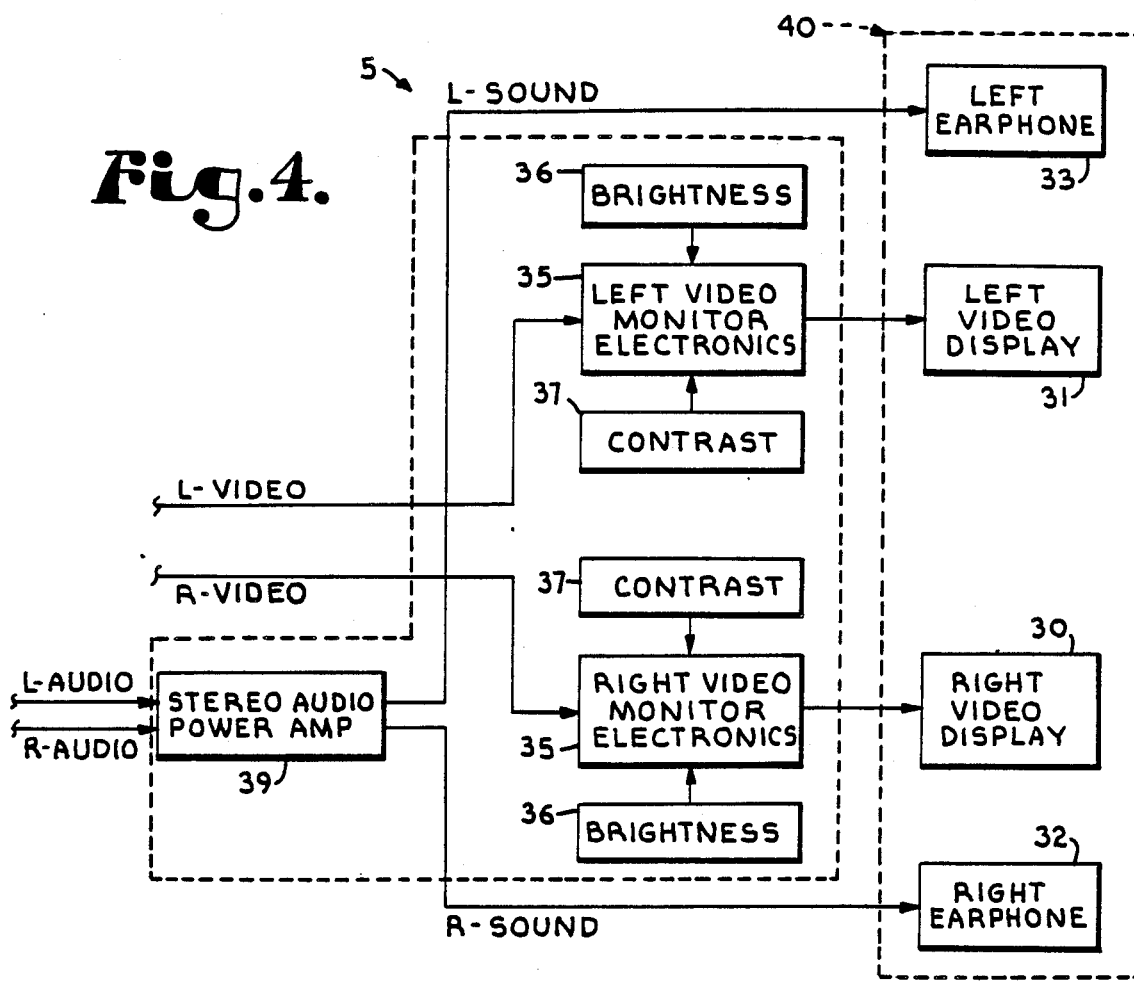
FIG. 4 is a block diagram of a stereo viewing and sound unit of the playback system.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail:

The reference numeral 1 generally designates a portable television playback system according to the present invention. The system 1 generally includes a video source unit 2 connected through video processing circuitry 3 and audio processing circuitry 4 to a stereo viewing and sound unit 5. The video source unit 2 may comprise a television receiver, a video tape unit 8 (FIG. 2), or a video disc player 9 (FIG. 3). Depending on the nature of the video source 2, the output signal therefrom might be separate video and audio signals, multiplexed video/audio signals, or right and left stereo components of multiplexed video/audio signals. The video and audio processing circuits 3 and 4 receive the output signals from the video source unit 2 and convert them to right and left video signals which may be identical or stereoscopic components and right and left audio signals which may be identical or stereophonic conponents for driving the stereo viewing and sound unit 5. The components of the system 1 are packaged for portability and are adapted to be powered by batteries, although an alternating current (AC) power supply may be provided for fixed base usage.

Referring to FIG. 2, an embodiment of the portable television playback system 1 is illustrated which is a tape player system 10. The video source unit 2 of the system 10 is a video tape player unit 8 which is preferably a videocassette player having miniaturized dimensions comparable to so-called "camcorders". The video tape player 8 is adapted to receive a videocassette such as the smaller versions of the standard videocassette cartridge formats. The video tape player 8 outputs a standard composite color video signal and a monaural or stereophonic audio signal. In the system 10, the video processing circuitry 3 takes the form of a video distributor 11 which is essentially a pair of identical video amplifiers which both receive the same input video signal and provide right and left video output signals for driving the right and left video components of the stereo viewing and sound unit 5. The audio processing circuitry 4 for the system 10 may be a similar type of audio distributor circuit 12 or preferably is a stereo preamplifier with a selectable monophonic mode for playing prerecorded tapes with either a monophonic sound track or stereophonic sound tracks.

Referring to FIG. 3, a preferred embodiment of the portable television playback system 1 is shown which is a video disc system 15. The preferred video source unit 2 for the system 15 is a stereo optical video disc playback unit 9. Briefly, the stereo video disc playback unit 9 is adapted to play video discs having two sides on which the right and left components of stereoscopic images and stereophonic sound are optically recorded on the opposite sides of the disc. On each side of the disc, the video and audio component signals are multiplexed and optically recorded as a spiral track. The output signals from the disc player 9 are right and left multiplexed video/audio signals. In the system 15, the video processing circuitry 3 includes a stereo video demultiplexer circuit 16 which receives the right and left video/audio signals and separates from them right and left video signals which are fed to the video components of the viewing and sound unit 5. Similarly, the audio processing circuitry 4 is a stereo sound demulitplexer circuit 17 which separates right and left audio signals from the video/audio signals for feeding to the audio components of the viewing and sound unit 5.

Figure 5:
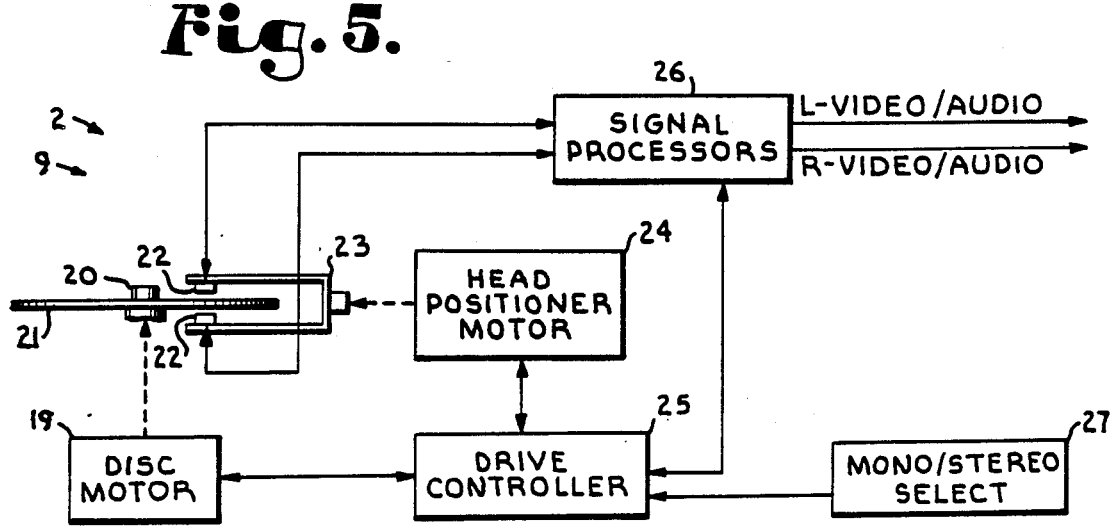
FIG. 5 is a block diagram of a stereo optical video disc player device according to the present invention.

FIG. 5 diagrammatically illustrates the principal components of a stereo optical video disc playback unit 9 which is suitable for the system 15. The unit 9 includes a rotary disc motor 19 for rotating a spindle 20 on which a stereo optical video disc 21 is positioned. A pair of optical read heads 22, of substantially conventional design, are positioned on a head positioner fork 23 which is movable radially of the disc 21 by a head positioner motor 24 of conventional design. The disc motor 19 and head positioner motor 24 are controlled by a drive controller circuit 25. The drive controller circuit 25 controls the drive motor 19 to maintain either a selected constant speed or such a rotational speed as to result in a constant linear speed of the tracks past the heads 22 depending on the manner in which the tracks are recorded. In addition, the controller 25 controls the head positioner motor 24 in such a manner as to follow the spiral tracks on the disc 21. The controller 25 is preferably adapted to control such functions as rapid access to portions of the program, speeded up motion, slow motion, and freeze frame or single frame display.

The signals as read by the heads 22 are fed to signal processor circuits 26 which cooperate with the drive controller 25 to maintain the proper disc rotation speed, proper head positioning, and proper focus of the read heads 22 in addition to preparing the multiplexed program signals for use by the demultiplexer circuits 16 and 17. While the optical disc playback unit 9 is primarily adapted for reading stereo optical discs having the right and left components on opposite sides of the disc 21, the unit 9 is also able to play monoscopically and monophonically recorded tracks on a single sided disc and on double sided discs without turning the disc over as is required in most conventional optical disc players. For this purpose, the unit 9 is provided with a mono/stereo selection switch 27 which is connected to the drive controller 25.

Referring to FIG. 4, a general diagram of the stereo viewing and sound unit 5 is illustrated. The unit 5 includes right and left video displays or image display devices 30 and 31 and right and left sound transducers or earphones 32 and 33. The image display devices 30 and 31 may be either black and white or, preferably, color cathode ray tubes (CRT's), liquid crystal displays (LCD's), or any other type of two dimensional image display devices. The image display devices 30 and 31 are driven by right and left video monitor circuits 35 whose configuration depends on the configuration of the display devices 30 and 31. If the displays are CRT's, the monitor circuits 35 generate and derive the required sweep, luminance, and chrominance signals from the right and left video signals. If the displays are LCD's, the monitor circuits generate the picture element or pixel addressing signals and color level signals. In most current high quality video sets, such functions as vertical and horizontal stability and linearity, color balance, and to an extent brightness and contrast are controlled automatically such that individual controls for these functions are not usually required. However, to allow for differences in individual perceptions, the quality of various program sources, and differing environments, a brightness control 36 and a contrast control 37 are included.

The right and left audio signals are fed to a stereo audio power amplifier 39 for driving the right and left earphones 32 and 33. The amplifier 39 preferably includes a volume control, a tone control, and a stereo balance control (not shown) for adjustments to the viewer's desires. Optically recorded sound programs are capable of very high fidelity. Therefore, the amplifier 39 and earphones 32 and 33 are preferably matched in quality for the fullest realization of such fidelity.

The amplifier 39 and video monitor circuits 35 are preferably housed in a single portable case (not shown)

along with the video source unit 2, the video processing circuitry 3, the audio processing circuitry 4, and a battery power supply (not shown). The term "portable" as used in reference to the system 1 is meant to convey the idea of easy to carry by a person of average size and strength. The remaining components of the viewing and sound unit 5 including the right and left image displays 30 and 31 and the right and left earphones 32 and 33 are mounted on a head worn unit 40 as will be detailed below.

Figure 6:
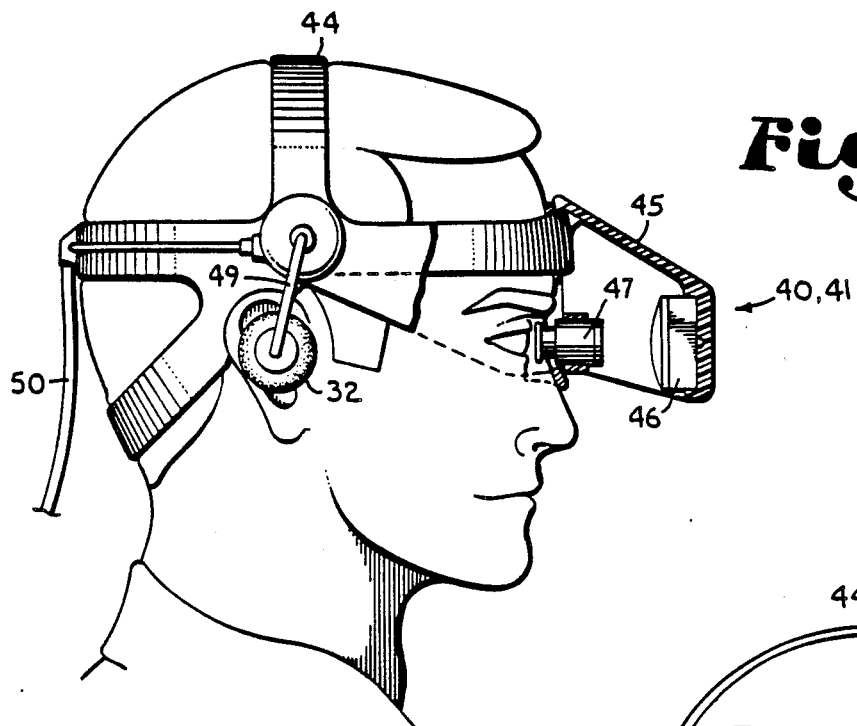
FIG. 6 is a side elevational view of a first embodiment of the stereo viewing and sound unit of the present invention employing liquid crystal displays as image display devices with a portion broken away to illustrate details.
Figure 7:
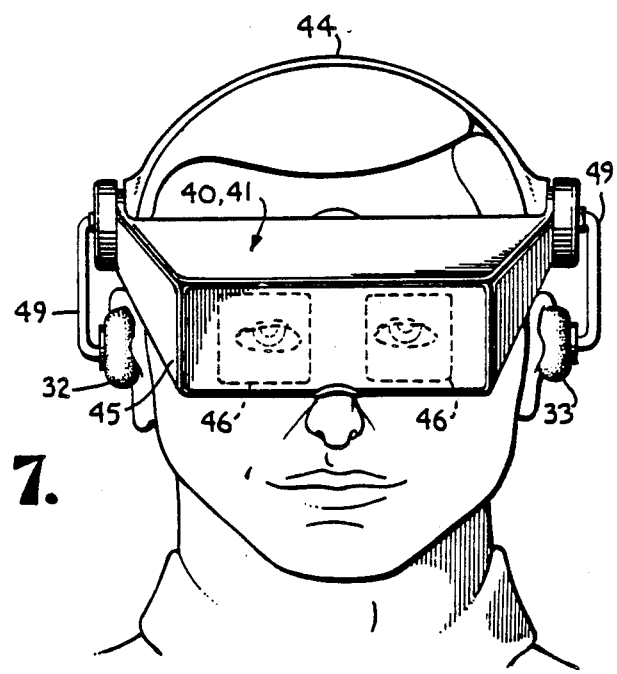
FIG. 7 is a front elevational view of the first embodiment of the stereo viewing and sound unit.
Figure 8:
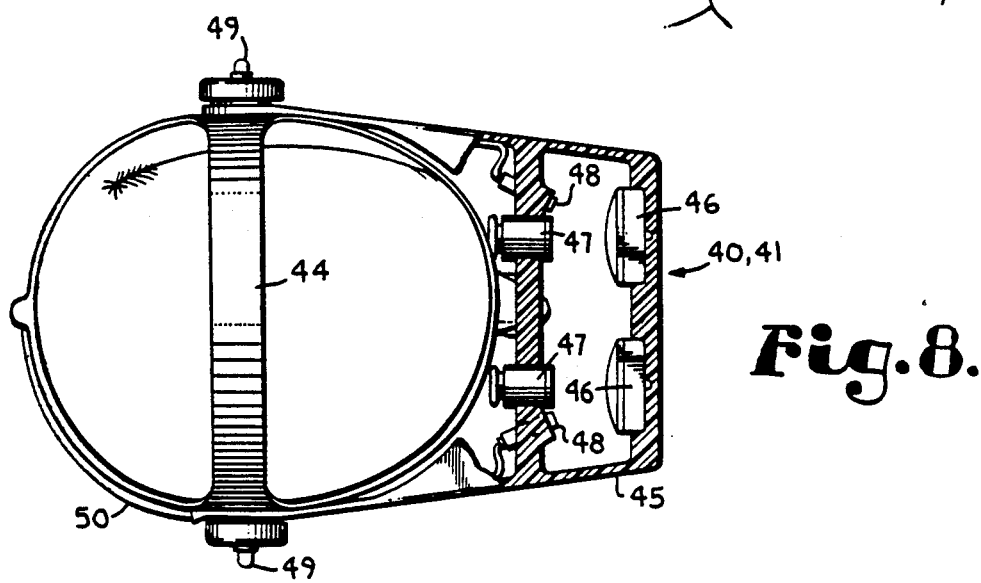
FIG. 8 is a top plan view of the first embodiment of the stereo viewing and sound unit with a portion broken away to illustrate details.

Referring to FIGS. 6, 7, and 8, a first embodiment of the head worn unit 40 is illustrated. The unit 41 includes a viewer unit support harness or headband 44 to which a visor 45 is pivotally connected. The harness 44 is preferably adjustable to the individual wearer. The visor 45 houses the right and left image display devices 30 and 31 which in the unit 41 comprise color LCD's 46. Also mounted in the visor 45 are optical elements 47 which compensate for the close positioning of the LCD's 46 to the viewer's eyes. Since LCD's are not self-luminous, it is necessary to provide light sources for viewing them such as the illustrated light sources 48. Alternatively, backlighting light sources could be provided. The right and left earphones 32 and 33 are mounted on the harness 44 as by suspending them on resilient rods 49. The signal carrying conductors from the video monitor circuits 35 and audio amplifier 39 are combined in a cable 50 which leads to the displays 46 and earphones 32 and 33. In non-entertainment uses such as in repairing devices, it might be desirable to be able to raise the visor 45 for a better view of the device being worked on.

FIG. 9 illustates a second embodiment 53 of the head worn viewing and sound unit 40. The unit 53 also includes a harness 54 which is similar in many respects to the harness 44 of the unit 41. The visor portion 55 of the unit 53 is somewhat different since the image display devices of the unit 53 are CRT's 56. The CRT's 56 are mounted by mounting bands 57 to the sides of the visor 55, and the images therefrom are reflected into the eyes of the viewer. The reflecting elements may be mirrors or prisms and, as illustrated, are Porro prisms having two internally reflecting surfaces 58 which result in upright and laterally correct images. The reflection of the images from the CRT's 56 is preferred to avoid the possibility of overexposure to X-rays therefrom because of the close spacing within the visor 55. Additional X-ray shielding material 59 is positioned about the CRT's 56 at least between the tubes 56 and the viewer. The head unit 53 includes optical elements 60 for comfortable focusing of the images from the CRT's 56. In most other respects, the head unit 53 is substantially similar to the head unit 41.

FIG. 10 illustrates a third embodiment 62 of the head unit 40 in the form of a pair of spectacles. The head unit 62 includes a spectacle frame 63 having a front eyeframe 64, and ear supports 65 hinged thereto. The eyeframe 64 has the right and left image displays mounted therein which are color LCD's 66. The LCD's 66 are backlighted by light sources 67 which are positioned forwardly of the LCD's 66. Optical elements 68 are positioned between the image displays 66 and the eyes of the viewer to compensate for the short focal distance available. The eyeframe 64 is formed in halves which are joined by a width adjustment mechanism 69 to accommodate various sized viewers. The sound transducers (not shown) are in the form used for spectacle mounted miniature hearing aids and are mounted within the ear supports 65. The sound is transmitted from the transducers to the viewer's ears by tubular earpieces 70. Since the weight of the image displays 66, backlights 67, and optical elements 68 might tend to affect the balance of the unit 62 as compared to conventional spectacles, a detachable rear headband 71 is preferably provided to help retain the unit 62 comfortably on the viewer's head while in use. The program signals are fed to the image displays and sound transducers by a cable 72 which may enter the unit 62 as through one of the ear supports 65.

It is to be understood that while certain forms of the present invention have been described and illustrated herein, it is not to be limited to the specific forms or arrangement of parts described and shown.

What is claimed and desired to be secured by Letters Patent is as follows:

1. A portable television playback system comprising:
   (a) a portable video source unit outputting a television signal having a video component and an audio component;
   (b) video processing circuitry receiving said television signal and deriving therefrom a right video signal and a left video signal;
   (c) audio processing circuitry receiving said television signal and deriving therefrom a right audio signal and a left audio signal; and
   (d) a viewing and sound unit having stereo capability including right and left video monitors and right and left sound transducers; said viewing and sound unit displaying images represented by said right and left video signals respectively on said right and left monitors and converting said right and left audio signals respectively to right and left audible sound signals through said right and left sound transducers.

2. A system as set forth in claim 1 wherein:
   (a) said portable video source unit is a portable video cassette tape player.

3. A system as set forth in claim 1 wherein:
   (a) said video source unit plays a stored video medium on which is recorded right and left components of a stereoscopic visual image; and
   (b) said stored video medium stores right and left components of stereophonically recorded sound.

4. A system as set forth in claim 1 wherein:
   (a) said portable video source unit is a portable, stereo optical video disc playback unit capable of reading an optical video disc on which are stored optically recorded representations of a stereoscopic image and stereophonic sound signals.

5. A system as set forth in claim 4 wherein said stereo optical video disc playback unit includes:
   (a) a rotary disc motor to rotate a stereo optical video disc;
   (b) a right head and a left head to optically read right and left tracks on a stereo optical video disc, said right and left tracks being optical recordations of multiplexed right and left video and audio signals respectively;
   (c) a head positioner motor mechanically connected to said right and left heads and operative to move said heads radially of said disc to read said right and left tracks respectively;
   (d) signal processor means connected to said right and left heads and operative to convert signals read by said heads respectively to right and left multiplexed video/audio signals; and (e) drive controller means having said disc motor, said head positioner motor, and said signal processor means connected thereto; said controller means being operative to cause said disc motor to rotate said disc at a selected speed and to cause said head positioner motor to position said right and left heads to follow said right and left tracks respectively.

6. A system as set forth in claim 5 wherein:
(a) said video processing circuitry includes a stereo video demultiplexer receiving said right and left multiplexed video/audio signals and separating therefrom a right video signal and a left video signal; and
(b) said audio processing circuitry includes a stereo sound demultiplexer receiving said right and left multiplexed video/audio signals and separating therefrom a right audio signal and a left audio signal.

7. A system as set forth in claim 1 wherein said stereo viewing and sound unit includes:
(a) a right two dimensional image display device and a left two dimensional image display device;
(b) right and left video monitor circuits connected respectively to said right and left image display devices, respectively receiving said right and left video signals, and displaying images represented respectively by said right and left video signals on said right and left display devices; and
(c) a stereo audio power amplifier connected to said right and left sound transducers, receiving said right and left audio signals, and converting same respectively to right and left sound signals through said right and left sound transducers.

8. A system as set forth in claim 7 wherein:
(a) each of said right and left image display devices is a two dimensional liquid crystal display device.

9. A system as set forth in claim 7 wherein:
(a) each of said right and left image display devices is a two dimensional color liquid crystal display device.

10. A system as set forth in claim 7 including:
(a) head harness means for wearing on the head of a user of said system;
(b) said image display devices being mounted on said harness in spaced apart relation;
(c) right and left optical transmission means mounted on said harness and including right and left lenses to respectively convey images from said image display devices to the right and left eyes of said user at comfortable focal distances; and
(d) said right and left sound transducers including right and left earphones mounted on said harness and positioned respectively at the right and left ears of said user wearing said harness.

11. A system as set forth in claim 10 wherein:
(a) each of said right and left image display devices is a two dimensional liquid crystal display device.

12. A system as set forth in claim 10 wherein:
(a) each of said right and left image display devices is a two dimensional color liquid crystal display device.

13. A system as set forth in claim 10 wherein:
(a) each of said right and left image display devices is a miniature color cathode ray tube; and
(b) each of said right and left optical transmission means includes an image reflector to reflect an image from said tube toward the respective eye of said user.

14. A system as set forth in claim 13 wherein said image reflector includes:
(a) a prism having at least one reflective surface.

15. A system as set forth in claim 13 wherein said image reflector includes:
(a) a Porro prism having two internally reflective surfaces.

16. A system as set forth in claim 10 wherein:
(a) said portable video source unit is a portable, stereo optical video disc playback unit capable of playing an optical disc on which are stored optically recorded representations of a stereoscopic image.

17. A portable television playback system comprising:
(a) a portable, stereo optical video disc unit capable of reading an optical video disc on which are stored optically recorded representations of a stereoscopic image and stereophonic sound signals and outputting right and left multiplexed video/audio signals;
(b) video processing circuitry receiving said multiplexed video/audio signals and separating therefrom respective right and left video signals;
(c) audio processing circuitry receiving said multiplexed video/audio signals and separating therefrom respective right and left audio signals;
(d) head harness means for wearing on the head of the user of said system;
(e) a right image display device and a left image display device, each of said image display devices being a two dimensional color liquid crystal display device and being mounted on said harness for viewing by a respective eye of said user;
(f) right and left video monitor circuits connected respectively to said right and left display devices, respectively receiving said right and left video signals, and displaying images represented respectively by said right and left signals on said right and left display devices;
(g) right and left earphones mounted on said harness and positioned respectively at the right and left ears of said user wearing said harness; and
(h) a stereo audio power amplifier connected to said right and left earphones, receiving said right and left audio signals, and converting same respectively to right and left sound signals through said right and left earphones.

18. A stereo optical video disc playback unit comprising:
(a) a rotary disc motor to rotate a stereo optical video disc;
(b) a right head and a left head to optically read right and left tracks on a stereo optical video disc, said right and left tracks being optical recordations of multiplexed right and left video and audio signals respectively;
(c) a head positioner motor mechanically connected to said right and left heads and operative to move said heads radially of said disc to read said right and left tracks respectively;
(d) signal processor means connected to said right and left heads and operative to convert signals read by said heads respectively to right and left multiplexed video/audio signals;
(e) drive controller means having said disc motor, said head positioner motor, and said signal processor means connected thereto; said controller means being operative to cause said disc motor to rotate said disc at a constant selected speed and to cause said head positioner motor to position said right and left heads to follow said right and left tracks respectively;

(f) a stereo video demultiplexer connected to said signal processor means and separating from said right and left multiplexed video/audio signals respective right and left video signals; and (g) a stereo sound demultiplexer connected to said signal processor means and separating from said right and left multiplexed video/audio signals respective right and left audio signals.

19. A unit as set forth in claim 18 wherein:

(a) said stereo optical video disc has opposite recorded sides with said right tracks recorded on one side thereof and said left tracks recorded on the other side; and (b) said right and left heads are positioned in opposition to read said right and left tracks on said opposite sides.

20. A unit as set forth in claim 18 wherein:

(a) said unit is portable.

21. In an optical video disc playback unit including a head positioned and movable to read an optically recorded signal on one side of an optical video disc, the improvement comprising:

(a) a pair of heads positioned in spaced apart relation on a single head positioner member which is movable is to simultaneously position said heads to read a first and a second track optically recorded at different positions on an optical video disc.

22. A unit as set forth in claim 21 wherein:

(a) said first and second tracks are right and left components of a stereoscopically recorded image.

* * * * *